United States Patent [19]

Gastinger

[11] Patent Number: 4,705,866

[45] Date of Patent: Nov. 10, 1987

[54] SYNTHESIS OF N-HALOGENATED PHENYL MALEIMIDE COMPOUNDS WITH TIN CONTAINING CATALYSTS

[75] Inventor: Robert G. Gastinger, Brookhaven, Pa.

[73] Assignee: Atlantic Richfield Company, Los Angeles, Calif.

[21] Appl. No.: 813,362

[22] Filed: Dec. 26, 1985

[51] Int. Cl.[4] ............... C07D 207/444; C07D 207/452
[52] U.S. Cl. .................................................. 548/549
[58] Field of Search ........................................ 548/549

[56] References Cited

U.S. PATENT DOCUMENTS 4,508,883 4/1985 Younas ................................ 526/262

FOREIGN PATENT DOCUMENTS 171593 2/1978 Czechoslovakia .
1174514 12/1969 United Kingdom ................ 548/549
1533068 11/1978 United Kingdom .

Primary Examiner—Glennon H. Hollrah
Assistant Examiner—D. B. Springer
Attorney, Agent, or Firm—Delbert E. McCaslin

[57] ABSTRACT

A process for the preparation of N-brominated or N-chlorinated phenylmaleimide by reacting maleic anhydride and a brominated or chlorinated aniline compound at temperatures of from about 100° C. to about 210° C. in the presence of tin containing catalyst compound and optionally an inert solvent.

12 Claims, No Drawings

SYNTHESIS OF N-HALOGENATED PHENYL MALEIMIDE COMPOUNDS WITH TIN CONTAINING CATALYSTS

BACKGROUND OF THE INVENTION

The present invention relates to a process for the preparation of N-halogenated phenyl maleimides, particularly N-brominated or N-chlorinated phenylmaleimide by reacting molten maleic anhydride with a brominated or chlorinated aniline at certain molar ratios in the presence of a tin (Sn) containing catalyst and optionally in the presence of an inert solvent.

A relatively few number of prior art processes have been proposed for the preparation of N-halogenated phenylmaleimide compounds and especially the N-brominated and N-chlorinated phenylmaleimides by catalytically reacting maleic anhydride with a halogenated aniline.

British Pat. No. 1,533,068 describes a process of preparing N-arylmaleimides including N-(chlorophenyl) maleimide by reacting maleic anhydride with an arylamine and then dehydrating the resulting N-arylmaleic acid amide for a cyclization in the presence of an acid catalyst in an inert solvent without separating the N-arylmaleic acid amide from the reaction mixture, the dehydration being carried out under conditions of azeotropic distillation.

Czechoslovakian Pat. No. 171,593 describes the preparation of halogenated derivations of N-phenylmaleimide at temperatures of 210° C. in the presence or absence of a zinc chloride catalyst.

U.S. Pat. No. 4,508,883 also describes the preparation of N-(2,4,6-tribromophenyl)maleimide by reacting 2,4,6-tribromoaniline and maleic anhydride in the presence of a zinc chloride catalyst.

The N-brominated or chlorinated phenyl maleimides prepared by the process of this invention are useful as fire retardant additives or for the formation of copolymers with, for example, bromostyrene as described in U.S. Pat. No. 4,508,883.

SUMMARY OF THE INVENTION

According to the present invention there is provided a novel process for the preparation of N-brominated or N-chlorinated phenylmaleimide compounds which comprises reacting maleic anhydride with a brominated or chlorinated aniline compound in the presence of an inorganic or organic tin containing compound and optionally in the presence of an inert solvent.

It is an object of this invention to provide a novel catalytic process for the preparation of N-brominated or N-chlorinate phenylmaleimide compound in high yield and conversion of reactants.

This and other objects and advantages of this invention will become apparent from the description of the invention which follows, and from the claims.

DETAILED DESCRIPTION OF THE INVENTION

In accordance with this invention an N-brominated or N-chlorinated phenylmaleimide having the formula:

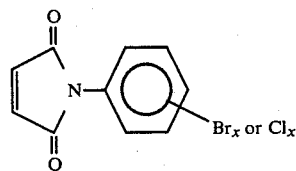

wherein each x separately represents an integer of from 1 to 5, is produced by reacting molten maleic anhydride and a brominated or chlorinated aniline such as 2,4,6-tribromoaniline or trichloroaniline at a temperature of from about 100° C. to about 210° C., preferably from about 120° to about 150° C. and at a molar ratio of maleic anhydride to the halogenated aniline of from about 1.0 to about 10.0:1.0 and preferably 1.5 to 2.5:1.0. in the presence of a catalyst or mixtures of catalysis comprising a tin (Sn) containing compound. The catalysts which are employed in the reaction mixture will be equivalent to between about 0.1 to about 100 weight percent and preferably from about 1.0 to about 10 weight percent based on the amount of halo-aniline employed.

The brominated or chlorinated aniline compounds used in the process of this invention may contain up to 5 Br or Cl groups and include the monobromo or monochloroanilines as well as the di-, tri-, tetra- and pentabromo or pentachloroanilines.

N-brominated phenylmaleimides and N-chlorinated phenylmaleimides produced by the process of this invention include N-(monobromophenyl and monochlorophenyl) malemides, N-(dibromophenyl and dichlorophenyl) maleimides, N-(tribromophenyl and trichlorophenyl) maleimides, N-(tetrabromophenyl and tetrachlorophenyl) maleimides and N-(pentabromophenyl and pentachlorophenyl) maleimides and mixtures thereof.

The reaction may be carried out in any suitable reactor which is generally equipped with a means for agitation and a means for regulating temperature. Although the order of addition of reactants, catalyst and solvent if any, may vary, a general procedure for carrying out the reaction is to charge the proper quantities of maleic anhydride and chlorinated or brominated aniline along with the desired tin containing catalyst into the reaction vessel and then heat the mixture to the desired temperature with stirring for the appropriate reaction period. The reaction may be carried out as a batch or continuous process and the reaction products recovered and treated by conventional methods such as filtration, extraction, etc.

The novel tin containing compound catalysts which may be employed in the process of the instant invention in the amounts hereinabove described include the tin(II) halides, $SnF_2$, $SnCl_2$, $SnBr_2$, $SnI_2$ the tin(IV) halides $SnF_4$, $SnlCl_4$, $SnBr_4$, $SnI_4$, tin(II) acetate ($Sn(CH_3CO_2)_2$), tin (II) 2-ethylhexanoate ($Sn(C_7H_{15}CO_2)_2$), tin oxalate ($Sn(C_2O_2)$), tin (IV) acetate ($Sn(CH_3CO_2)_4$), triorganotin halides having the formulae $R_3SnX$, $R_2R'SnX$ or $RR'R''SnX$ wherein R, R' and R'' is methyl, ethyl, propyl, butyl etc., phenyl or benzyl and X is F, Cl, Br or I, diorganotin halides having the formula $R_2SnX_2$ or $RR'SnX_2$ wherein R, R' and X are as hereinabove described, and monoorganotin halides having the formula $RSnX_3$ wherein R is as hereinabove described, as well as dialkyltin oxides ($R_2SnO$)

wherein R is an alkyl group having 1 to 10 carbon atoms.

The process of the present invention as generally carried out at atmospheric pressure or the autogenous pressure of the reaction system, although higher pressures of up to about 10 atmospheres may be employed and especially at the higher reaction temperatures. Subatmospheric pressures may be employed, if desired.

The reaction time is generally dependent on the N-bromo or chloro phenylmaleimide being produced, the reaction temperature and catalyst employed and will vary depending on whether the process is continuous or batch, but will generally range between about 0.2 to about 4.0 hours and usually between 1 and 2 hours.

Although solvents are not required in the reaction, solvents or mixtures of solvents which are stable and substantially chemically inert to the components of the reaction system may be employed if desired. Suitable solvents which may be used include, for example, aromatic and haloaromatic hydrocarbons such as benzene, toluene, ethylbenzene, xylenes, mesitylene, cumene, chlorobenzene, dichlorobenzene, chlorotoluene as well as ethylbenzene, dibutybenzenes nitrobenzene, ethylene dichloride, propylene dichloride, trichloroethylene, tetrachloroethylene; $C_5$ to $C_{18}$ aliphatic and cycloaliphatic hydrocarbons such as pentane, methylpentane, heptane, hexane, octane, nonane, cyclohexane, cyclopentane, dodecane, pentadecane, octadecane, cyclooctane as well as "Tetralin" and "Decalin" and the like; ketones such as acetone, methylethyl ketone, methylisopropyl ketone and the like; benzonitrile, tetrahydrofuran and the like.

The following examples are provided to illustrate the invention in accordance with the principles of this invention, but are not to be construed as limiting the invention in any way except as indicated by the appended claims.

EXAMPLE I

A mixture of 2,4,6-tribromoaniline (1.20g, 3.64 mmol), maleic anhydride (0.83g, 8.5 mmol) and tin(II) chloride (0.064g, 0.34 mmol) is heated to 142° C. with mixing and held at this temperature for 1.9 hours. The reaction mixture is cooled, extracted with xylene, filtered and the resulting filtrate water washed. Solvent removal yielded N-(2,4,6-tribromophenyl)maleimide. Analysis by High Pressure Liquid Chromatography (HPLC) showed conversion of 2,4,6-tribromoaniline to be 99.9% and selectivity to N-(2,4,6-tribromophenyl)-maleimide based on reacted 2,4,6-tribromoaniline of 75.0%.

EXAMPLE 2

A mixture of 2,4,6-trichloroaniline (1.20g, 6.11 mmol), maleic anhydride (0.80g, 8.2 mmol) and tin(II) chloride (0.068g, 0.36 mmol) is heated to 140° C. with mixing and held at this temperature for 2.0 hours. The reaction mixture is cooled, extracted with xylene, filtered and the resulting filtrate water washed. Solvent removal yielded N-(2,4,6-trichlorophenyl)maleimide. HPLC analysis showed conversion of 2,4,6-trichloroaniline was 96.4% and selectivity to N-(2,4,6-trichlorophenyl)maleimide based on reacted 2,4,6-trichloroaniline was 88.0%.

EXAMPLES 3–5

In Examples 3 to 5 which follow in Table form, the general procedure of Examples 1 and 2 was repeated using 2,4,6-tribromoaniline with various catalysts and conditions. Results are summarized in the Table I.

TABLE

| Example No. | Catalyst | Temp. °C. | MAN/TBA Mole ratio | Catalyst (wt. %)* | Time (hrs.) | Conv. (%) | Sel. (%) |
|---|---|---|---|---|---|---|---|
| 3 | Sn(CH$_3$CO$_2$)$_2$[1] | 140 | 2.30 | 6.2 | 2.0 | 96.0 | 70.3 |
| 4 | SnBr$_2$ | 142 | 2.32 | 6.5 | 2.0 | 97.5 | 78.0 |
| 5 | Sn(C$_6$H$_5$)$_3$Cl[2] | 141 | 2.34 | 7.1 | 2.0 | 92.0 | 70.0 |

*Catalyst percent by weight based on 2,4,6-tribromoaniline employed
MAN = maleic anhydride
TBA = 2,4,6-tribromoaniline
Conv. = Conversion
Sel. = Selectivity
[1] = tin(II) acetate
[2] = triphenyltin chloride

What is claimed is:

1. A process for the preparation of an N-brominated or N-chlorinated phenylmaleimide having the formula

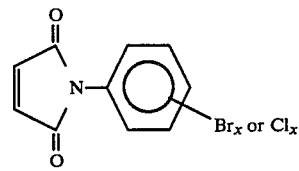

wherein each x separately represents an integer of 1 to 5 which comprises reacting at a temeprature from about 100° C. to about 210° C., maleic anhydride with a brominated or chlorinated aniline at a molar ratio of anhydride to aniline of from about 1.0 to 10.0:1.0 in the presence of from about 0.1 about 100 weight percent of a tin containing catalyst compound based on the amount of brominated or chlorinated aniline employed and being selected from the group consisting of tin (II) halides, tin (IV) halides, tin (II) acetate, tin (II) 2-ethyhexanoate, tin oxalate, tin (IV) acetate, triorganotin halides having the formulae R$_3$SnX, R$_2$R'SnX or RR'R"SnX, diorganotin halides having the formulae R$_2$SnX$_2$ or RR'SnX$_2$, and monoorganotin halides having the formula RSnX$_3$ wherein R, R' and R" is methyl, ethyl, propyl, butyl, phenyl or benzyl and X is F, Cl, Br or I, and dialkyltin oxides having the formula (R$_2$SnO) wherein R is an alkyl group having from 1 to 10 carbon atoms.

2. A process according to claim 1 wherein the reaction temperature is in the range of from about 120° to about 150° C.

3. A process according to claim 1 wherein the catalyst is employed in an amounts of from 1.0 to about 10 weight percent based on the brominated or chlorinated aniline employed.

4. A process according to claim 1 wherein the brominated aniline is 2,4,6-tribromoaniline.

5. A process according to claim 1 wherein the chlorinated aniline is 2,4,6-trichloroaniline.

6. A process according to claim 1 wherein the molar ratio of maleic anhydride to brominated aniline is 1.5 to 2.5:1.0.

7. A process according to claim 1 wherein the catalyst is selected from the group consisting of tin(II) chloride, tin(II) bromide, tin(II) acetate and triphenyltin chloride.

8. A process according to claim 7 wherein the catalyst is tin(II) chloride.

9. A process according to claim 7 wherein the catalyst is tin(II) acetate.

10. A process according to claim 6 wherein the catalyst is triphenyltin chloride.

11. A process according to claim 1 wherein the reaction is carried out in the presence of a solvent.

12. A process for the preparation of N-2,4,6-(tribromophenyl)maleimide having the formula:

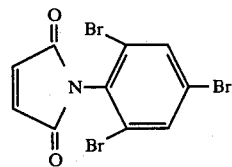

which comprises reacting at a temperature of from about 120° C. to about 150° C. maleic anhydride with 2,4,6-tribromoaniline at a molar ratio of anhydride to aniline of from 1.5 to 2.5:1 in the presence of from about 1.0 to about 10 percent by weight based on the amount of brominated aniline employed of a tin containing catalyst compound or mixtures thereof and being selected from the group consisting of tin (II) halides, tin (IV) halides, tin (II) acetate, tin (II) 2-ethyhexanoate, tin oxalate, tin (IV) acetate, triorganotin halides having the formulae $R_3SnX$, $R_2R'SnX$ or $RR'R''SnX$, diorganotin halides having the formulae $R_2SnX_2$ or $RR'SnX_2$, and monoorganotin halides having the formula $RSnX_3$ wherein R, R' and R'' is methyl, ethyl, propyl, butyl, phenyl or benzyl and X is F, Cl, Br or I, and dialkyltin oxides having the formula $(R_2SnO)$ wherein R is an alkyl group having from 1 to 10 carbon atoms.

* * * * *